US 11,464,584 B2

(12) United States Patent
De Wijs et al.

(10) Patent No.: US 11,464,584 B2
(45) Date of Patent: Oct. 11, 2022

(54) INTERVENTIONAL DEVICE WITH PIEZOELECTRIC TRANSDUCER

(71) Applicant: KONINKLIJKE PHILIPS N.V., Eindhoven (NL)

(72) Inventors: Willem-Jan Arend De Wijs, Oss (NL); Cornelis Gerardus Visser, Eindhoven (NL); Hendrik Roelof Stapert, Eindhoven (NL); Johannes Wilhelmus Weekamp, Beek en Donk (NL); Gerardus Franciscus Cornelis Maria Lijten, Veldhoven (NL); Eric Franciscus Johannes Claessens, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/970,974

(22) PCT Filed: Feb. 3, 2019

(86) PCT No.: PCT/EP2019/052560
§ 371 (c)(1),
(2) Date: Aug. 19, 2020

(87) PCT Pub. No.: WO2019/162065
PCT Pub. Date: Aug. 29, 2019

(65) Prior Publication Data
US 2020/0397512 A1  Dec. 24, 2020

(30) Foreign Application Priority Data
Feb. 21, 2018  (EP) .................................... 18157815

(51) Int. Cl.
*A61B 34/20* (2016.01)
*A61B 8/08* (2006.01)
(Continued)

(52) U.S. Cl.
CPC .......... *A61B 34/20* (2016.02); *H01L 41/0475* (2013.01); *H01L 41/1132* (2013.01); (Continued)

(58) Field of Classification Search
CPC .... A61B 2034/2063; A61B 2034/2072; A61B 2090/3929; A61B 34/20; A61B 8/0841; (Continued)

(56) References Cited

U.S. PATENT DOCUMENTS

| 4,911,172 A | * | 3/1990 | Bui ........................ A61B 8/12 600/461 |
| 6,585,763 B1 | * | 7/2003 | Keilman .................. A61B 8/06 623/1.42 |

(Continued)

FOREIGN PATENT DOCUMENTS

| WO | 2017013224 A1 | 1/2017 |
| WO | 2017102369 A1 | 6/2017 |

OTHER PUBLICATIONS

PCT/EP2019/052560 ISR & WO, Feb. 3, 2019, 12 Page Document.
(Continued)

*Primary Examiner* — Oommen Jacob
*Assistant Examiner* — Maria Christina Talty

(57) ABSTRACT

An interventional device includes an elongate shaft and a transducer strip. The transducer strip includes a first edge and an opposing second edge. The first edge and the second edge are separated by a width dimension, and the first edge and the second edge each extend along a length direction of the transducer strip. The transducer strip also includes a piezoelectric transducer that extends along a transducer direction that forms an acute angle with respect to the length direction. The transducer strip is wrapped in the form of a spiral around the elongate shaft of the interventional device such that the piezoelectric transducer forms a band around
(Continued)

the elongate shaft. The width dimension is defined such that the adjacent first and second edges of consecutive turns of the spiral abut or overlap one another.

15 Claims, 5 Drawing Sheets

(51) Int. Cl.
*A61M 25/01* (2006.01)
*H01L 41/047* (2006.01)
*H01L 41/113* (2006.01)
*A61B 90/00* (2016.01)
*A61B 8/00* (2006.01)

(52) U.S. Cl.
CPC ........... *A61B 8/0841* (2013.01); *A61B 8/4488* (2013.01); *A61B 2034/2063* (2016.02); *A61B 2034/2072* (2016.02); *A61B 2090/3929* (2016.02); *A61M 25/0108* (2013.01); *A61M 2025/0166* (2013.01)

(58) Field of Classification Search
CPC ... A61B 8/4245; A61B 8/4483; A61B 8/4488; A61M 2025/0166; A61M 25/0108; H01L 41/0475; H01L 41/1132
See application file for complete search history.

(56) References Cited

U.S. PATENT DOCUMENTS

| | | | |
|---|---|---|---|
| 2009/0251028 A1* | 10/2009 | Vilkomerson | B06B 1/06 29/25.35 |
| 2015/0182187 A1* | 7/2015 | Samset | A61B 8/463 600/424 |
| 2016/0081657 A1* | 3/2016 | Rice | A61B 8/445 600/301 |
| 2016/0100768 A1* | 4/2016 | Someya | A61B 5/296 600/393 |
| 2016/0374710 A1* | 12/2016 | Sinelnikov | A61B 8/481 600/439 |
| 2017/0112528 A1* | 4/2017 | Crisman | A61B 17/3423 |
| 2017/0136231 A1* | 5/2017 | Kelly | A61N 1/0587 |
| 2018/0207683 A1* | 7/2018 | De Wijs | B06B 1/0688 |

OTHER PUBLICATIONS

Mung et al: "A Non-Disruptive Technology for Robust 3D Tool Tracking for Ultrasound F-Guided Interventions": MICCAI 2011, Part i, LNCS 6891, pp. 153-160.

* cited by examiner

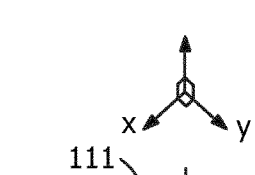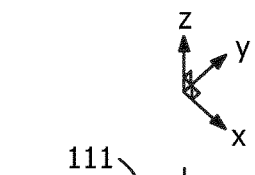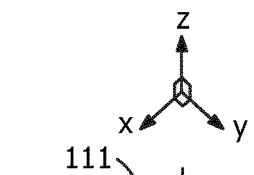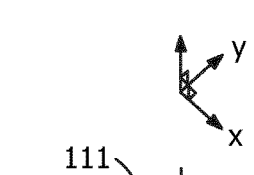
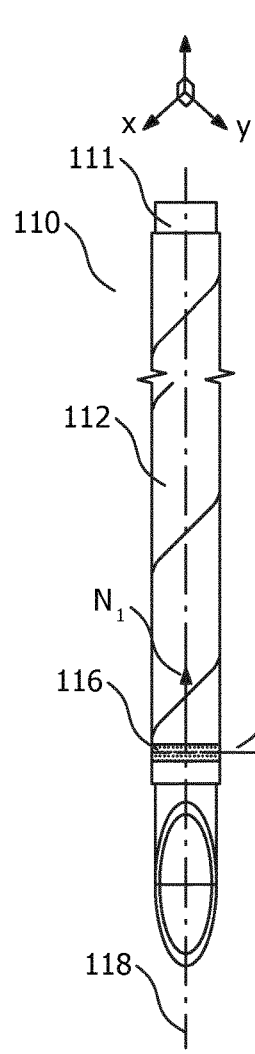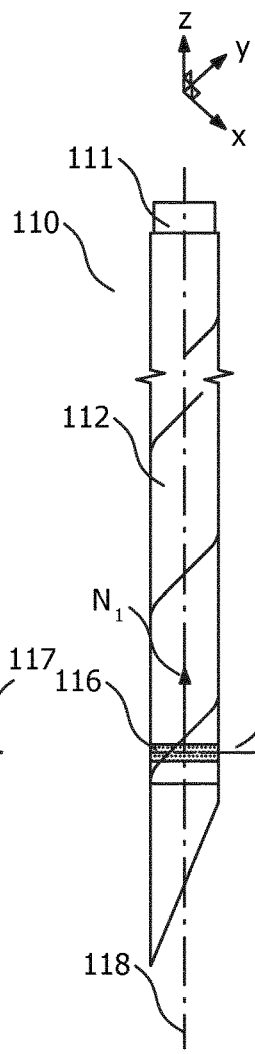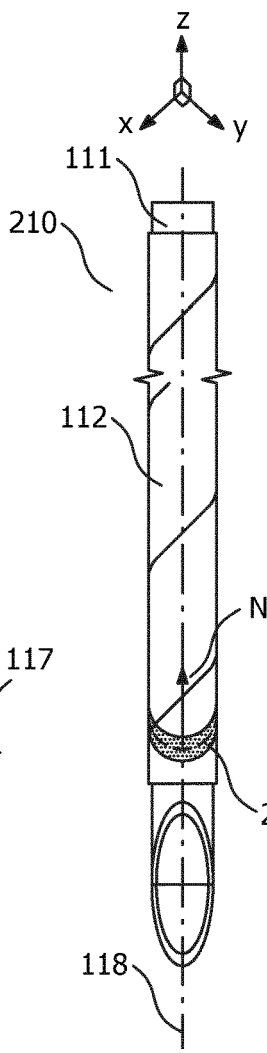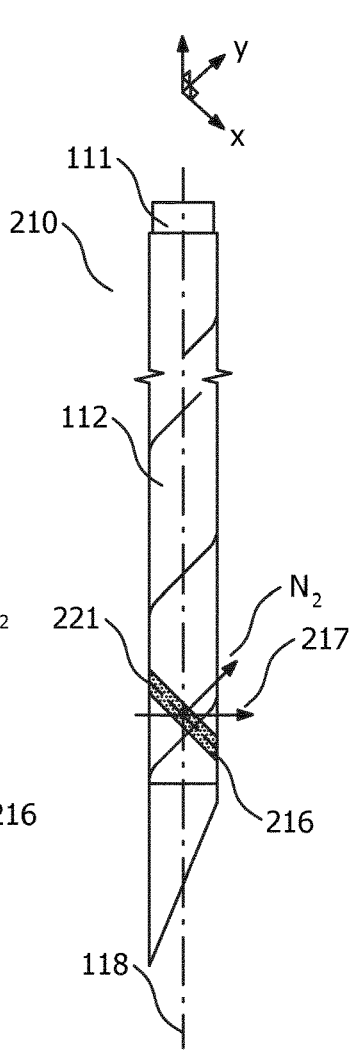
FIG. 1A　　FIG. 1B　　FIG. 2A　　FIG. 2B
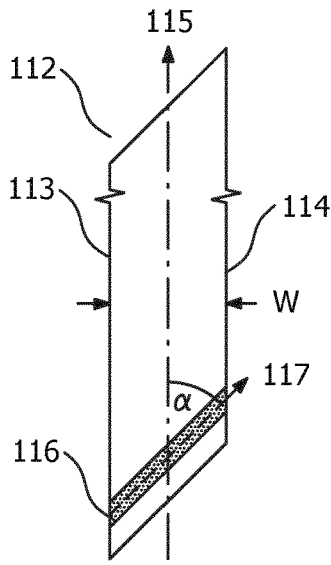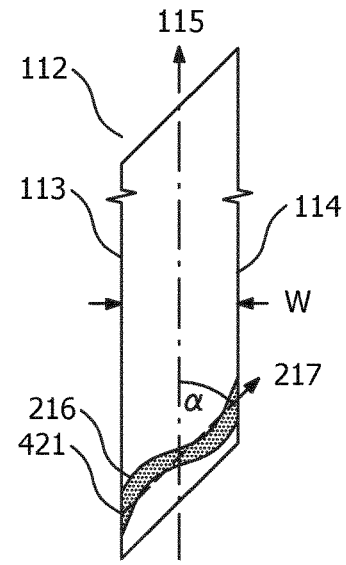
FIG. 3　　FIG. 4

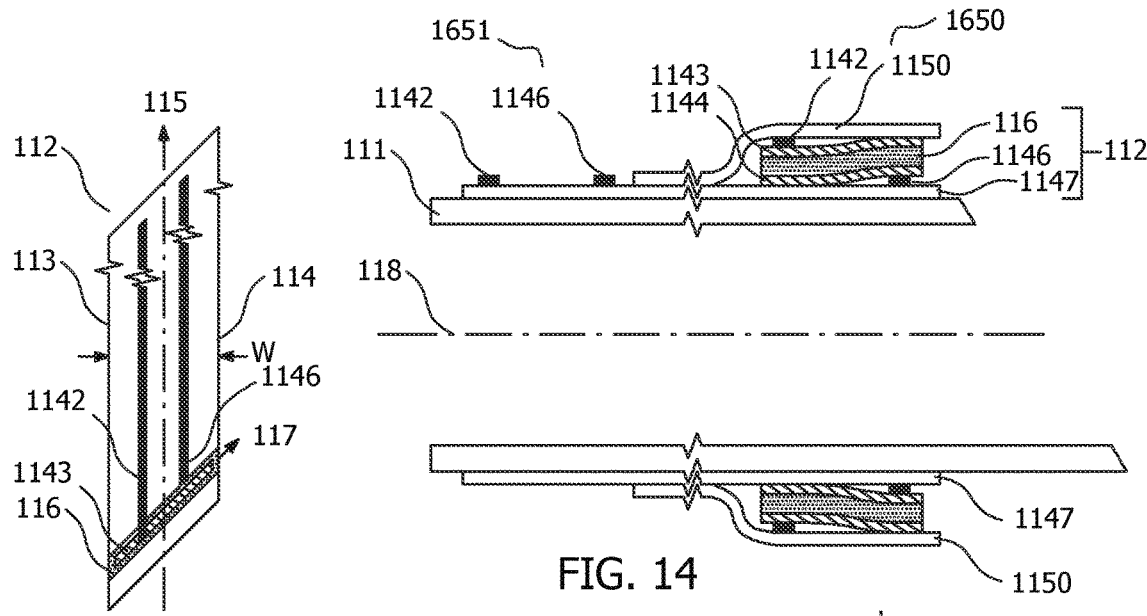
FIG. 13
FIG. 14
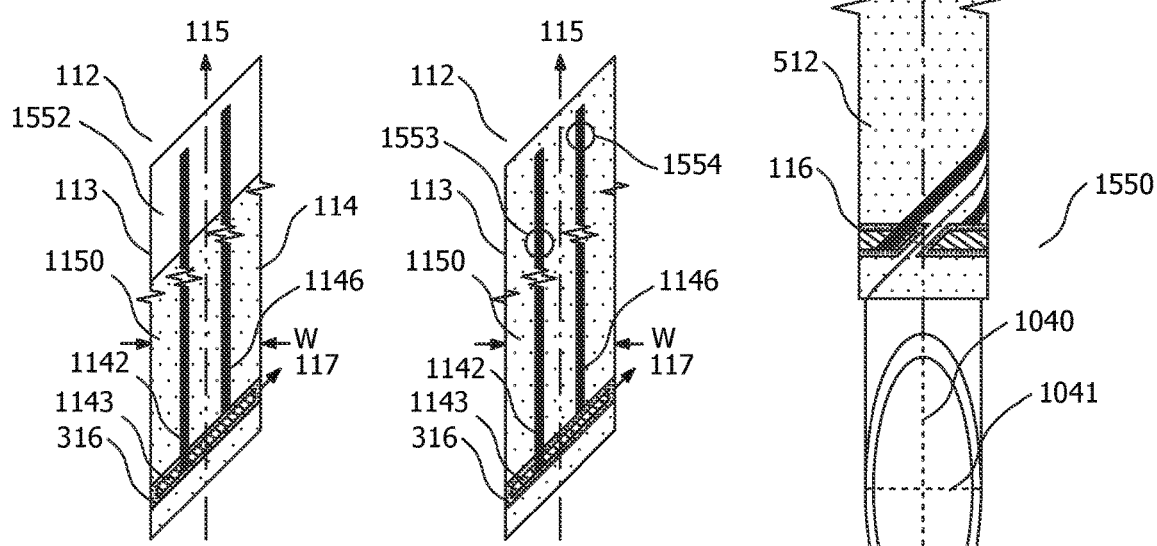
FIG. 16A
FIG. 16B
FIG. 15

INTERVENTIONAL DEVICE WITH PIEZOELECTRIC TRANSDUCER

CROSS-REFERENCE TO PRIOR APPLICATIONS

This application is the U.S. National Phase application under 35 U.S.C. § 371 of International Application No. PCT/EP2019/052560, filed on Feb. 3, 2019, which claims the benefit of European Patent Application No. 18157815.4, filed on Feb. 21, 2018. These applications are hereby incorporated by reference herein.

FIELD OF THE INVENTION

The invention relates to an interventional device with a piezoelectric transducer. The piezoelectric transducer may operate as a sensor or as an actuator. The interventional device may be used in various interventional procedures in the medical field. In one contemplated application the piezoelectric transducer may be used to track a position of the interventional device respective an ultrasound field of a beamforming ultrasound imaging probe.

BACKGROUND OF THE INVENTION

Interventional procedures in the medical field increasingly use sensing and actuation to gain more information about, or to treat, a patient's anatomy. Piezoelectric materials are sometimes used in these applications due to the wide range of transducer functions they offer. Specific, non-limiting examples include the transducing, i.e. conversion of signals from one form of energy to another, of ultrasound, acoustic, vibration, and thermal energy. Such transducers may be used in a wide range of applications including ultrasound imaging, blood flow monitoring, heart rate determination, temperature monitoring, and high frequency ultrasound "HIFU" treatment. In one exemplary application described in a document by Mung, J., et al. "A Non-disruptive Technology for Robust 3D Tool Tracking for Ultrasound-Guided Interventions" in Fitchinger, G., Martel, A., Peters, T., (Eds.) MICCAI 2011, Part I, LNCS, Vol. 6891, pp. 153-160, Springer, Heidelberg (2011), an ultrasound-based position determination system is described in which a ultrasound sensor mounted on a needle is used to detect the ultrasound signals from a beamforming ultrasound imaging probe. The needle may be tracked in ultrasound-guided interventions from routine needle insertion for regional anesthesia, to biopsies and percutaneous ablation of cancer, and to more advanced procedures such as structural heart repair.

An issue commonly faced in such applications is that of attaching a piezoelectric transducer to an interventional device. In one solution to this problem, document WO2017013224 describes a transducer laminate in which electrical contact is made between electrical conductors and a transducer layer. In one implementation the transducer laminate is wrapped around an elongate device in the form of a spiral.

Another document WO2017102369A1 relates to an apparatus for tracking a position of an interventional device respective an image plane of an ultrasound field. The position includes an out-of-plane distance. A geometry-providing unit includes a plurality of transducer-to-distal-end lengths, each length corresponding to a predetermined distance between a distal end of an interventional device and an ultrasound detector attached to the interventional device, for each of a plurality of interventional device types. An image fusion unit receives data indicative of the type of the interventional device being tracked; and based on the type: selects from the geometry-providing unit, a corresponding transducer-to-distal-end length; and indicates in a reconstructed ultrasound image both the out-of-plane distance and the transducer-to-distal-end length for the interventional device within the ultrasound field.

In spite of such solutions there remains room to improve the attachment of piezoelectric transducers to interventional devices.

SUMMARY OF THE INVENTION

The present invention seeks to improve the attachment of a piezoelectric transducer to an interventional device. Thereto, an interventional device is provided that includes an elongate shaft and a transducer strip. The transducer strip includes a first edge and an opposing second edge, the first edge and the second edge being separated by a width dimension. The first edge and the second edge each extend along a length direction of the transducer strip. A piezoelectric transducer that is disposed on the transducer strip extends along a transducer direction that forms an acute angle with respect to the length direction of the transducer strip. The transducer strip is wrapped in the form of a spiral around the elongate shaft of the interventional device such that the piezoelectric transducer forms a band around the elongate shaft. Moreover, the width dimension is defined such that the adjacent first and second edges of consecutive turns of the spiral abut or overlap one another.

In so doing the spiral wrapping provides a simple method of attaching the piezoelectric transducer to the elongate shaft of the interventional device. The interventional device may for example be rolled across the transducer strip and attached to the interventional device by means of an adhesive. The abutting or overlapping adjacent turns of the spiral act to provide, respectively, a smooth outer surface to the interventional device and thereby lower resistance to insertion in a body, and avoid the exposure of material underlying the wrapped transducer strip.

In one aspect the elongate shaft extends along a shaft axis and the piezoelectric transducer is defined by a straight line. Moreover, the transducer direction is arranged perpendicularly to the shaft axis such that the band lies in a plane having a normal that is co-axial with the shaft axis. In so doing a transducer is provided that has a sensitivity or emission profile that has reduced sensitivity to a rotational angle about the shaft axis.

In another aspect the elongate shaft extends along a shaft axis and the piezoelectric transducer is defined by a sinusoidal shape that oscillates about a centerline. The centerline is a straight line defined by the transducer direction. The transducer direction is arranged perpendicularly to the shaft axis such that the band lies in a plane having a normal that is tilted with respect to the shaft axis. In so doing a transducer is provided that has a predefined variation in sensitivity or emission profile with rotational angle.

In another aspect the piezoelectric transducer includes a first end and a second end. Moreover, the band formed by the wrapped transducer strip includes either i) an overlap or ii) a space between the first end and the second end. The overlap or space provides for a distinctive transducer sensitivity, or emission, at rotational angles about the shaft axis that correspond to the overlap or space. This aspect may be used in determining the rotational angle of the interventional device. The interventional device may for example include a bevel that is defined by an ellipse having a major axis and a minor axis. The major axis defines two major rotational angles at two opposing positions around a circumference of the elongate shaft, and the minor axis defines two minor rotational angles at two opposing positions around the circumference of the elongate shaft. Moreover, the overlap or the space includes a midpoint that is aligned rotationally around the circumference of the elongate shaft at one of the major rotational angles or at one of the minor rotational angles. In so doing the overlap or space is defined respective the bevel. The distinctive sensitivity or emission at rotational angles corresponding to the overlap or space may be used to identify the rotational angular position of the bevel.

Further aspects and beneficial effects are described with reference to the appended claims. Moreover, further advantages from the described invention will also be apparent to the skilled person.

BRIEF DESCRIPTION OF THE FIGURES

FIG. 1 illustrates an interventional device 110 that includes a transducer strip 112 with a piezoelectric transducer 116, in each of two orthogonal projections (A) and (B).

FIG. 2 illustrates another interventional device 210 that includes a transducer strip 112 with a piezoelectric transducer 216, in each of two orthogonal projections (A) and (B).

FIG. 3 illustrates an exemplary transducer strip 112 that includes piezoelectric transducer 116 disposed thereon.

FIG. 4 illustrates another exemplary transducer strip 112 that includes piezoelectric transducer 216 disposed thereon.

FIG. 13 illustrates transducer strip 112 that, in addition to the items of FIG. 11 further includes second electrode 1144 and second electrical conductor 1146.

FIG. 14 illustrates a distal end of an elongate shaft 111 of an interventional device that includes piezoelectric transducer 116 and two electrical conductors disposed on the transducer strip.

FIG. 15 illustrates an interventional device 1510 that includes distal end 1550 and proximal end 1551.

FIG. 16 illustrates two exemplary transducer strips 112 that each include first electrical conductor 1142 and second electrical conductor 1146 and in which a portion of first electrical conductor 1142 and second electrical conductor 1146 are both exposed for making electrical contact to an external connector.

DETAILED DESCRIPTION OF THE INVENTION

Figure 5:
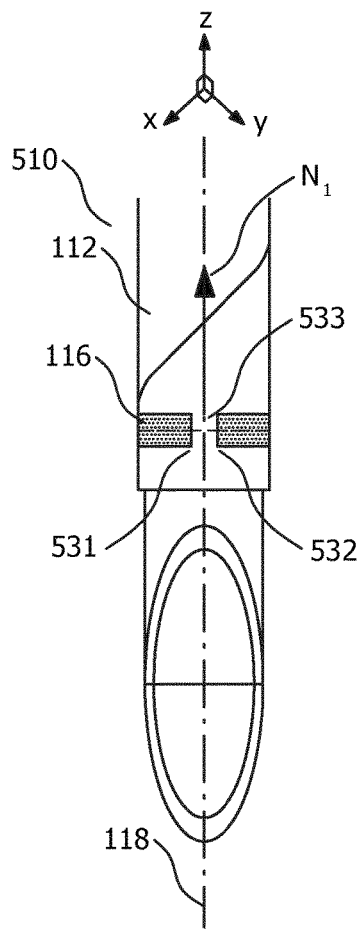
FIG. 5 illustrates a portion of an interventional device 510 that includes a transducer strip 112 with a piezoelectric transducer 116 that has a first end 531 and a second end 532 which forms a wrapped band that includes a space 533 between the first end 531 and the second end 532.

In order to illustrate the principles of the present invention an interventional device is described with particular reference to an exemplary position determination application in which the piezoelectric transducer disposed on the interventional device is an ultrasound transducer that is used to determine position of the interventional device respective the ultrasound field of a beamforming ultrasound imaging system. It is however to be appreciated that this positioning, or tracking, application is only exemplary and that the interventional device may also be used in various sensing and actuation applications in the medical field. These may include for example blood flow monitoring, heart rate monitoring, ultrasound imaging, thermometry, and various ultrasound-based treatments. Reference is made to an interventional device in the form of a needle, however it is also to be appreciated that the invention finds application with other types of interventional devices having an elongate shaft such as a catheter, a biopsy device, a guidewire, a heart valve (re)placement tool, a pacemaker lead, an intravenous line or a surgical tool in general. Moreover, the interventional device may be used in a wide variety or medical procedures from routine needle insertion for regional anesthesia, to biopsies and percutaneous ablation of cancer, and to more advanced procedures such as structural heart repair.

Thereto, FIG. 1 illustrates an interventional device 110 that includes a transducer strip 112 with a piezoelectric transducer 116, in each of two orthogonal projections (A) and (B). In FIG. 1, a medical needle is illustrated as an example of interventional device 110. The medical needle has a bevel that is shown in each of two orthogonal projections (A) and (B); however, as mentioned above, the medical needle simply serves as an example and the invention is not limited to medical needles or indeed beveled devices. With reference to FIG. 1, interventional device 110 includes elongate shaft 111 and transducer strip 112. Piezoelectric transducer 116 is disposed on transducer strip 112, and transducer strip 112 is wrapped in the form of a spiral around elongate shaft 111 such that piezoelectric transducer 116 forms a band around elongate shaft 111.

FIG. 3 illustrates an exemplary transducer strip 112 that includes piezoelectric transducer 116 disposed thereon. The arrangement of FIG. 1 may be obtained by wrapping the exemplary transducer strip 112 of FIG. 3 around elongate shaft 111 of the medical needle illustrated in FIG. 1. With reference to FIG. 3, transducer strip 112 includes first edge 113 and opposing second edge 114, these edges being separated by a width dimension W. First edge 113 and second edge 114 each extend along length direction 115 of transducer strip 112. Length direction 115 is orthogonal to the direction in which width dimension W is measured. Transducer strip 112 includes piezoelectric transducer 116 that extends along transducer direction 117. Transducer direction 117 forms an acute angle, α, with respect to length direction 115 of transducer strip 112. When the exemplary transducer strip 112 of FIG. 3 is wrapped in the form of a spiral around elongate shaft 111 of the medical needle illustrated in FIG. 1, piezoelectric transducer 116 forms a band around the elongate shaft 111. Moreover, in FIG. 1, width dimension W is defined such that the adjacent first and second edges 113, 114 of consecutive turns of the spiral abut or overlap one another.

In order for consecutive turns of the spiral to abut, i.e. just touch, one another, the following equation should be satisfied:

$$W = \pi \cdot D \cdot \sin(\alpha) \qquad \text{Equation 1}$$

wherein α is the acute angle defined by the transducer direction 117, 217 with respect to length direction 115, and D is the diameter of elongate shaft 111. By arranging that W exceeds the above value, consecutive turns of the spiral overlap one another. Preferably the overlap is a fraction of width W, for example 1-10% of width W. Consequently by arranging that:

$$W \geq \pi \cdot D \cdot \sin(\alpha) \qquad \text{Equation 2}$$

it is ensured that there are no gaps between adjacent first and second edges 113, 114 of consecutive turns of the spiral.

Consequently the spiral wrapping arrangement of FIG. 1 provides a simple method of attaching piezoelectric transducer 116 to elongate shaft 111 of interventional device 110. The interventional device may for example be rolled across the transducer strip and attached to the interventional device by means of an adhesive. Alternatively the transducer strip may be rotated about a fixed elongate shaft and likewise attached to the interventional device by means of an adhesive. The abutting or overlapping adjacent turns of the spiral in FIG. 1 act to provide, respectively, a smooth outer surface to interventional device 110 and thereby lower resistance to insertion in a body, and avoid the exposure of material underlying the wrapped transducer strip. In the case of abutting adjacent turns the smooth topography may for example reduce the trapping of debris during insertion of the exemplary medical needle. In the case of overlapping adjacent turns the ease of sterilizing the interventional device may be improved by avoiding the exposure of material underlying the wrapped transducer strip.

Transducer strip 112 may be formed using a variety of processes. In a preferred embodiment transducer strip 112 includes a polymer film which is illustrated as having an exemplary rhomboidal outline in FIG. 3. Whilst the rhomboidal outlined polymer film illustrated in FIG. 3 may be wrapped around elongate shaft 111 such that the ends of wrapped transducer strip 112 lie in a plane having a normal that is defined by shaft axis 118, transducer strips with other outlines are also contemplated, including for example a rectangular outline. The polymer film may be formed from a variety of polymer materials including Polyethylene terephthalate (PET), Polyimides (PI), Polyamides (PA).

Piezoelectric transducer 116 may be formed from a variety of piezoelectric materials. Both hard and soft piezoelectric materials are contemplated. Moreover, whilst illustrated as being a single piezoelectric element, piezoelectric transducer 116 may be alternatively be formed from multiple separate elements that are either electrically connected together in one or more groups. Flexibility of piezoelectric transducer 116 may be improved through the use of multiple elements that are arranged in this way, and may be particularly advantageous when hard piezoelectric materials are used. Preferably, piezoelectric transducer 116 is formed from a layer of Polyvinylidene fluoride, i.e. PVDF, or a layer of PVDF co-polymer such as polyvinylidene fluoride trifluoroethylene (P(VDF-TrFE)) or a layer of PVDF terpolymer such as P(VDF-TrFE-CTFE). The exemplary PVDF layer may be disposed on a layer of pressure sensitive adhesive, i.e. PSA coated PET to form transducer strip 112 in FIG. 3, or for example laminated between two of more such PSA-coated layers. Pressure sensitive adhesives are a class of materials that form an adhesive bond upon application of pressure. Sheets of such pressure sensitive adhesives include product 2811CL made by the 3M Corporation™. These may be supplied as PSA-coated polymer sheets such as product 9019 supplied by the 3M Corporation™. In one contemplated fabrication technique, a strip of PVDF is adhesively attached to PSA-coated sheet and cut into multiple pieces, each of which correspond to transducer strip 112. Other fabrication techniques are also contemplated, including the use of molding techniques, the use of sol gel deposition processes for making PVDF layers on polymer films, and the adhesive attachment of pre-fabricated discrete hard-piezoelectric elements to a polymer film.

With further reference to FIG. 3 and FIG. 1, elongate shaft 111 in FIG. 1 extends along shaft axis 118. Also, piezoelectric transducer 116 is defined by a straight line. Moreover, in one implementation, transducer direction 117, along which piezoelectric transducer 116 extends is arranged perpendicularly to shaft axis 118 such that the band lies in a plane having a normal $N_1$ that is co-axial with the shaft axis 118. In so doing, piezoelectric transducer 116 has a sensitivity or emission profile that has reduced sensitivity to a rotational angle about the shaft axis. In the exemplary position determination application, details of which are provided later, the piezoelectric transducer 116 receives ultrasound signals from a beamforming ultrasound probe. The detected ultrasound signals are used to determine the position of piezoelectric transducer 116 respective the various beams of the beamforming ultrasound probe. The position of piezoelectric sensor 116 is subsequently displayed in an ultrasound image provided by the beamforming ultrasound probe. Due to difficulties in locating piezoelectric sensor at the tip of interventional device 118, the actual tip position is inferred based on the displayed position of piezoelectric sensor 116. By minimizing the sensitivity of piezoelectric transducer 116 to rotational angle about shaft axis 118, the actual tip position likewise remains in a more reliable position respective the displayed position of piezoelectric transducer 116.

FIG. 2 illustrates another interventional device 210 that includes a transducer strip 112 with a piezoelectric transducer 216, in each of two orthogonal projections (A) and (B). In FIG. 2, elongate shaft 111 extends along a shaft axis 118. However, in contrast to FIG. 1, in FIG. 2, piezoelectric transducer 216 forms a band that is tilted with respect to shaft axis 118. With further reference to FIG. 4, which illustrates another exemplary transducer strip 112 that includes piezoelectric transducer 216 disposed thereon, the arrangement of FIG. 2 may be achieved by wrapping transducer strip 112 of FIG. 4 around elongate shaft 111 of the medical needle illustrated in FIG. 2. With reference to FIG. 4, piezoelectric transducer 216 has a sinusoidal shape that oscillates about centerline 421. Centerline 421 is a straight line defined by transducer direction 217. Moreover, transducer direction 217 is arranged perpendicularly to the shaft axis 118 such that the band lies in a plane 221 having a normal $N_2$ that is tilted with respect to the shaft axis 118. Corresponding items in FIG. 2 and FIG. 1, and FIG. 4 and FIG. 3, share the same labels. Moreover transducer strip 112 in FIG. 4 may be formed using the same methods as described with reference to FIG. 3. Transducer strip 112 in FIG. 2 may be attached to elongate shaft 111 in the same manner as described with reference to FIG. 1. With further reference to FIG. 4, transducer direction 217 also forms an acute angle, α, with respect to length direction 115 of transducer strip 112. However, when transducer strip 112 of FIG. 3 is wrapped in the form of a spiral around elongate shaft 111 of the medical needle illustrated in FIG. 2, the sinusoidal shape of piezoelectric transducer 216 forms the tilted band illustrated in FIG. 2. The angle of the tilt may be adjusted by varying the amplitude of the sinusoidal shape. Moreover the start and end points of the band may be determined by adjusting a phase shift of the sinusoidal shape.

In so doing the piezoelectric transducer of FIG. 2 provides a characteristic variation in sensitivity or emission profile with rotational angle. Returning to the exemplary application of position determination described above, the predetermined variation in sensitivity or emission profile may be used to improve determination of the position of the actual tip position of the interventional device respective the displayed transducer position. If a user of the FIG. 2 interventional device rotates the interventional device by, for example one quarter turn, the position of the displayed transducer will move accordingly by a known distance along shaft axis 118. By so turning the interventional device the user can thus better gauge the distance from the displayed transducer to the tip of the interventional device. For example, one quarter turn might correspond to one eighth of the distance from the distance from the displayed transducer to the tip of the interventional device. This feature may therefore assist a user of the interventional device in accurately determining its position.

In some implementations the piezoelectric transducer may include an overlap or a space between two of its ends. The overlap or space may introduce a rotational dependence to the sensitivity or emission profile of the piezoelectric transducer around shaft axis 118. When there is an overlap the sensitivity may be increased due to the increased thickness of piezoelectric transducer at rotational angles corresponding to the overlap. When there is a space the sensitivity may be decreased at rotational angles corresponding to the space. The overlap or space may for example be disposed along a line that is parallel to, or at an acute angle with respect to shaft axis 118. The overlap or space may for example occupy between 1 and 5 degrees of rotation, or between 1 and 10 degrees of rotation, or between 1 and 20 degrees of rotation. The overlap or space may assist in identifying the rotational angle of the interventional device about its shaft axis 118.

Thereto, FIG. 5 illustrates a portion of an interventional device 510 that includes a transducer strip 112 with a piezoelectric transducer 116 that has a first end 531 and a second end 532 which forms a wrapped band that includes a space 533 between the first end 531 and the second end 532. With reference to the exemplary position determination application in which piezoelectric transducer 116 receives ultrasound signals from a beamforming ultrasound probe, space 533 in FIG. 5 may provide a range of rotational angles with reduced sensitivity to ultrasound signals. By rotating interventional device 510 about its shaft axis 118 a user can determine the rotational orientation of interventional device 510 via the dip in received signal strength that coincides with the space.

In FIG. 5, ends 531, 532 of piezoelectric transducer 116 are illustrated as being parallel to shaft axis 118. By so-shaping ends 531, 532, a high contrast in received ultrasound signal strength can be achieved between a rotational position coincident with the center of space 533 and rotational positions away from the space. Increasing the rotational angular range of the space also helps to improve this contrast.

Figure 7:
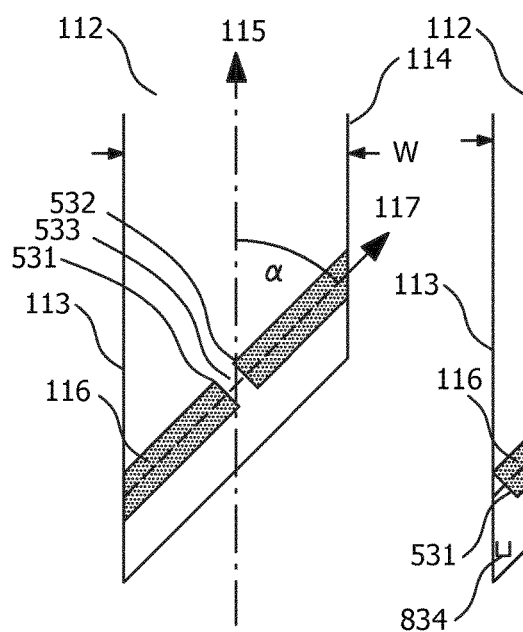
FIG. 7 illustrates a first example of a transducer strip 112 that may be used to provide a space 533 between a first end 531 and a second end 532 of piezoelectric transducer 116 when transducer strip 112 is wrapped in the form of a spiral around the elongate shaft 111 of an interventional device.
Figure 8:
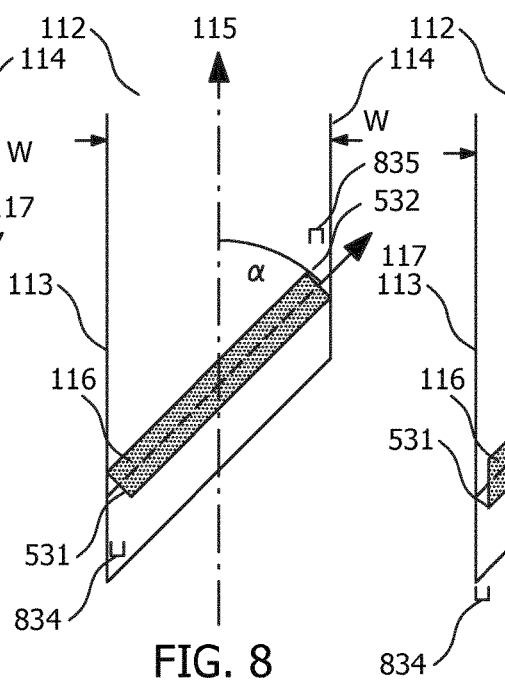
FIG. 8 illustrates a second example of a transducer strip 112 that may be used to provide a space 533 between a first end 531 and a second end 532 of piezoelectric transducer 116 when transducer strip 112 is wrapped in the form of a spiral around the elongate shaft 111 of an interventional device.

FIG. 7 illustrates a first example of a transducer strip 112 that may be used to provide a space 533 between a first end 531 and a second end 532 of piezoelectric transducer 116 when transducer strip 112 is wrapped in the form of a spiral around the elongate shaft 111 of an interventional device. Transducer strip 112 of FIG. 7 includes space 533 along the length of piezoelectric transducer 116 and may be used to obtain the arrangement illustrated in FIG. 5. The two separate elements of piezoelectric transducer 116 may be electrically connected together in order to operate as a single transducer. In so doing, space 533 illustrated in FIG. 5 may be provided at a rotational angle that does not coincide with the abutting or overlapping edges 113, 114 of transducer strip 112. FIG. 8 illustrates a second example of a transducer strip 112 that may be used to provide a space 533 between a first end 531 and a second end 532 of piezoelectric transducer 116 when transducer strip 112 is wrapped in the form of a spiral around the elongate shaft 111 of an interventional device. In contrast to the example of FIG. 7 the example in FIG. 8 includes a continuous piezoelectric transducer 116 and space 533 may be provided at a rotational angle that does coincide with the abutting or overlapping edges 113, 114 of transducer strip 112.

In FIG. 8 first end 531 of piezoelectric transducer 116 is disposed adjacent first edge 113 of transducer strip 112, second end 532 is disposed adjacent second edge 114, and piezoelectric transducer 116 includes a first gap 834 between first end 531 of piezoelectric transducer 116 and first edge 113 of transducer strip 112 and second gap 835 between second end 532 of piezoelectric transducer 116 and second edge 114 of transducer strip 112. Either or both of first gap 834 and second gap 835 may be present. In so doing, transducer strip 112 in FIG. 8 may be used to provide space 633 in FIG. 6 that includes at least a portion of first gap 834 and/or at least a portion of second gap 835.

Figure 6:
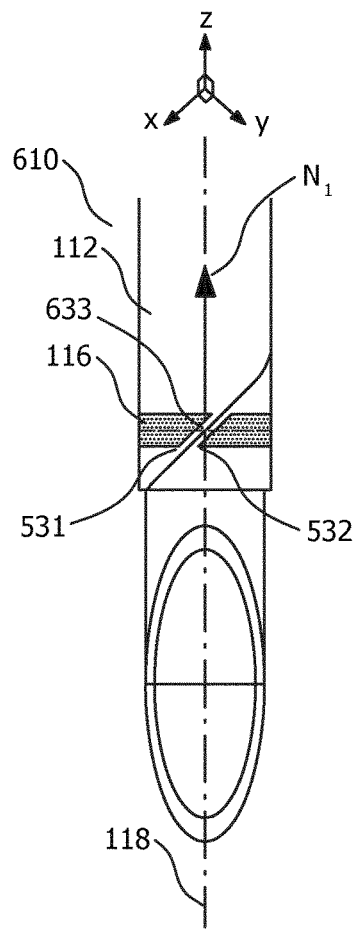
FIG. 6 illustrates a portion of an interventional device 610 that includes a transducer strip 112 with a piezoelectric transducer 116 that has a first end 531 and a second end 532 which forms a wrapped band that includes a space 633 between the first end 531 and the second end 532.

In another implementation a space may be provided along a line that is at an acute angle with respect to shaft axis 118. By so-shaping ends 531, 532, as compared to the example of FIG. 5, a reduced contrast in received ultrasound signal strength can be achieved between a rotational position coincident with the center of space 633 and rotational positions away from the space. Thereto, FIG. 6 illustrates a portion of an interventional device 610 that includes a transducer strip 112 with a piezoelectric transducer 116 that has a first end 531 and a second end 532 which forms a wrapped band that includes space 633 between first end 531 and second end 532. The arrangement of FIG. 6 may for example be obtained by using the transducer strip 112 illustrated in FIG. 9, which illustrates a third example of a transducer strip 112 that may be used to provide space 633 between first end 531 and second end 532 of piezoelectric transducer 116 when transducer strip 112 is wrapped in the form of a spiral around the elongate shaft 111 of an interventional device.

Figure 9:
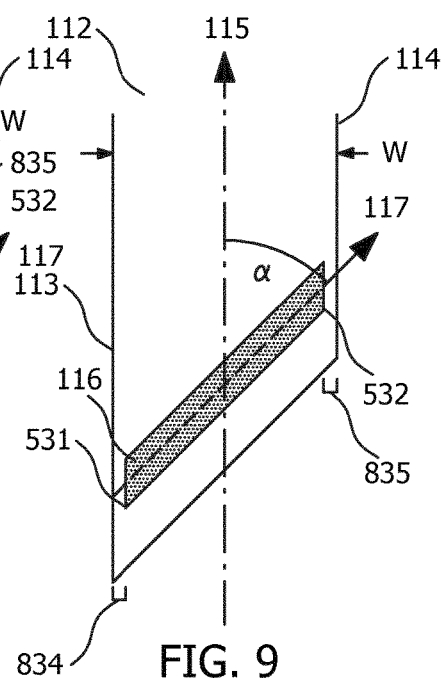
FIG. 9 illustrates a third example of a transducer strip 112 that may be used to provide a space 633 between a first end 531 and a second end 532 of piezoelectric transducer 116 when transducer strip 112 is wrapped in the form of a spiral around the elongate shaft 111 of an interventional device.

As an alternative to spaces 533, 633 described above, an overlap may be achieved with the arrangements of FIG. 5 and FIG. 6 by using the transducer strips of FIGS. 7-9 and ensuring that when the transducer strip is wrapped in the form of a spiral around elongate shaft 111 such that adjacent first and second edges 113, 114 of consecutive turns of the spiral overlap one another, that there is sufficient overlap for ends 532, 532 of piezoelectric transducer 116 to overlap one another.

Figure 10A:
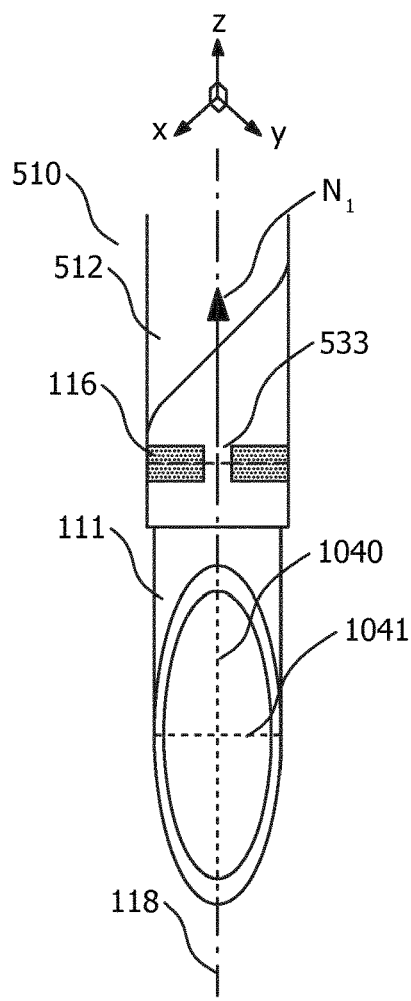
FIG. 10 illustrates a portion of interventional device 510 that includes a bevel in side-view (A) and in cross-section view (B).
Figure 10B:
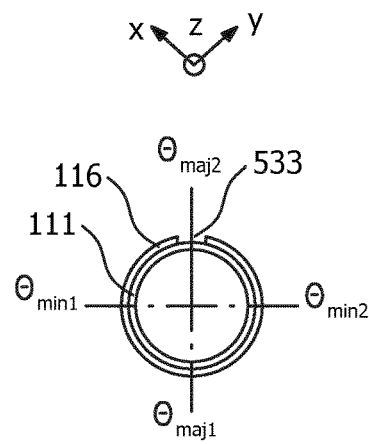

In some implementations the interventional device may include a characteristic feature disposed at a predetermined rotational angle about elongate shaft 111, such as a bevel, a tissue-receiving notch of a biopsy device, a leg of a mitral clip for repairing a mitral heart valve, and so forth. The bevel may for example be that of a catheter, a cannula or a needle. Moreover, the above-described overlap or space 533, 633 may be provided at a rotational angle that coincides with the predetermined rotational angle respective the bevel. With reference to the exemplary position determination application in which piezoelectric transducer 116 receives ultrasound signals from a beamforming ultrasound probe, the distinctive sensitivity at rotational angles corresponding to the space or overlap may allow a user to determine a rotation of the bevel of the interventional device about its shaft axis 118. Thereto, FIG. 10 illustrates a portion of interventional device 510 that includes a bevel in side-view (A) and in cross-section view (B). With reference to FIG. 10A and FIG. 10B, the bevel is defined by an ellipse having a major axis 1040 and a minor axis 1041. Major axis 1040 defines two major rotational angles $\theta_{maj1}$, $\theta_{maj2}$ at two opposing positions around a circumference of elongate shaft 111 and minor axis 1041 defines two minor rotational angles $\theta_{min1}$, $\theta_{min2}$ at two opposing positions around the circumference of the elongate shaft 111. Moreover, overlap or the space 533, 633 includes a midpoint that is preferably aligned rotationally around the circumference of the elongate shaft 111 at one of the major rotational angles $\theta_{maj1}$, $\theta_{maj2}$ or at one of the minor rotational angles $\theta_{min1}$, $\theta_{min2}$. In so doing, the distinctive sensitivity at rotational angles corresponding to the space or overlap can be used to identify a particular rotational orientation of the bevel. This may for example be useful in some so-called "bevel-up" medical procedures when it is desirable to direct the bevel outwards and towards the patient's skin and thus towards an ultrasound probe that emits ultrasound signals. Alternatively it may be desirable to minimize the rotational sensitivity of the piezoelectric transducer by performing a bevel-up procedure with the space or overlap positioned diametrically opposite the bevel and therefore, in use, directed away from the received ultrasound signals where the distinctive sensitivity has minimal impact on the detected ultrasound signals.

Figure 11:
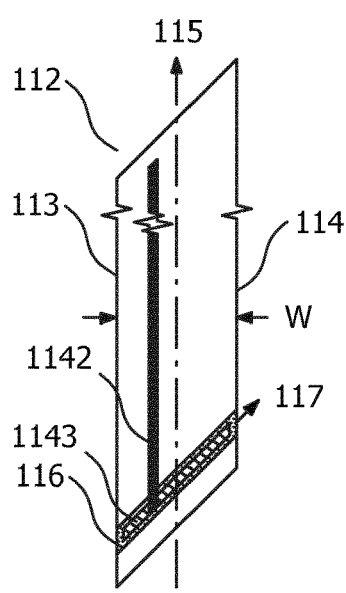
FIG. 11 illustrates transducer strip 112 that includes first electrical conductor 1142 that is in electrical contact with piezoelectric transducer 116.

Transducer strip 112 may also include various electrical connections that may be used to convey detected electrical signals between a piezoelectric transducer that is disposed toward, i.e. relatively closer to, a distal end of the interventional device, and an interconnection region towards, i.e. relatively closer to a proximal end of the interventional device. Thereto, FIG. 11 illustrates transducer strip 112 that includes first electrical conductor 1142 that is in electrical contact with piezoelectric transducer 116. Transducer strip 112 in FIG. 11 may be wrapped around the elongate axis of an interventional device. First electrical conductor 1142 extends along the length direction 115 of transducer strip 112. An additional electrical shield layer not shown in FIG. 11 may be included on top of first electrical conductor 1142, the two being separated by an insulating layer. This shield layer may reduce electromagnetic interference either to or from other electrical equipment.

Figure 12:
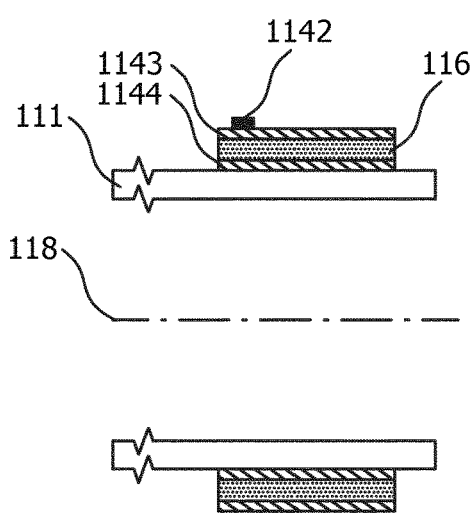
FIG. 12 illustrates a distal end of an elongate shaft 111 of an interventional device that includes piezoelectric transducer 116.

FIG. 12 illustrates a distal end of elongate shaft 111 of an interventional device that includes piezoelectric transducer 116. The arrangement of FIG. 12 may be achieved by wrapping transducer strip 112 of FIG. 11 around elongate shaft 111 of an interventional device, as illustrated e.g. in FIG. 10A. In FIG. 12, piezoelectric transducer 116 further includes first electrode 1143. First electrical conductor 1142 is in electrical contact with piezoelectric transducer 116 via first electrode 1143. This arrangement helps in reducing the contact or "spreading" resistance between first electrical conductor 1142 and piezoelectric transducer 116.

With continued reference to FIG. 12, piezoelectric transducer 116 also includes second electrode 1144 and elongate shaft 111 of the interventional device is formed from a conductive material. Moreover, second electrode 1144 is in electrical contact with conductive elongate shaft 111. In so doing, electrical contact to piezoelectric transducer can be achieved with a single electrical conductor 1142 disposed on transducer strip 112; its other electrical connection being made via the conductive interventional device.

FIG. 13 illustrates transducer strip 112 that, in addition to the items of FIG. 11 further includes second electrode 1144 and second electrical conductor 1146. Second electrical conductor 1146 extends along length direction 115 of transducer strip 112, and second electrical conductor 1146 is in electrical contact with piezoelectric transducer 116 via second electrode 1144. FIG. 13 provides an alternative arrangement to the single electrical trace of FIG. 11 and may offer reduced interference on transducer signals detected by piezoelectric transducer 116 or reduced interference to nearby electrical equipment as a result of electrical signals carried to piezoelectric transducer 116. FIG. 14 illustrates a distal end of an elongate shaft 111 of an interventional device that includes piezoelectric transducer 116 and two electrical conductors disposed on the transducer strip. The FIG. 14 interventional device includes the wrapped transducer strip 112 of FIG. 13.

In some implementations an interventional device may include a transducer strip 112 that has electrical conductors that are exposed towards the distal end of the interventional device in order to make an electrical contact to an external connector. Thereto, FIG. 15 illustrates an interventional device 1510 that includes distal end 1550 and proximal end 1551. Piezoelectric transducer 116 is disposed towards distal end 1550 of interventional device 1510. Moreover, first electrical conductor 1142 and second electrical conductor 1146 each extend along the along length direction 115 of transducer strip 112 to proximal end 1551. Towards; i.e. relatively closer to, proximal end 1551 of interventional device 1510, first electrical conductor 1142 and second electrical conductor 1146 are both exposed along at least a portion of elongate shaft for making electrical contact to an external connector.

FIG. 16 illustrates two exemplary transducer strips 112 that each include first electrical conductor 1142 and second electrical conductor 1146 and in which a portion of first electrical conductor 1142 and second electrical conductor 1146 are both exposed for making electrical contact to an external connector. The exemplary transducer strips of FIG. 16 may be wrapped in the form of a spiral around the elongate shaft 111 of an interventional device, as illustrated in FIG. 15. With reference to FIGS. 14-16, transducer strip 112 includes polymer substrate 1147 that is to be arranged innermost with respect to the interventional device 1510 and polymer superstrate 1150 that is to be arranged outermost with respect to the elongate shaft 111 of interventional device 1510. Towards distal end 1550 of interventional device 1510, first electrical conductor 1142 and second electrical conductor 1146 are sandwiched between polymer substrate 1147 and polymer superstrate 1150. Towards proximal end 1551 of interventional device 1510 polymer superstrate 1150 includes at least one opening 1552, 1553, 1554 for exposing first electrical conductor 1142 and/or second electrical conductor 1146 along the at least a portion of elongate shaft 111.

The exemplary transducer strip 112 of FIG. 16B includes separate openings 1553, 1554 for each electrical conductor 1142, 1146. Towards proximal end 1551 of the interventional device 1510 polymer superstrate 1150 includes first opening 1553 that exposes the first electrical conductor 1142 and second opening 1554 that exposes second electrical conductor 1146. First opening 1553 and second opening 1554 are staggered along length direction 115 of transducer strip 112 such that first electrical conductor 1142 and second electrical conductor 1146 are exposed at axially-separated axial positions along elongate shaft 111 of interventional device 1510 and at the same rotational angle around a circumference of elongate shaft 111. The arrangement of FIG. 15 and the transducer strip of FIG. 16B allow selective exposure of a portion of the electrical conductors such that contact to a flat surface of e.g. a printed circuit board may be achieved at this portion.

Figure 17:
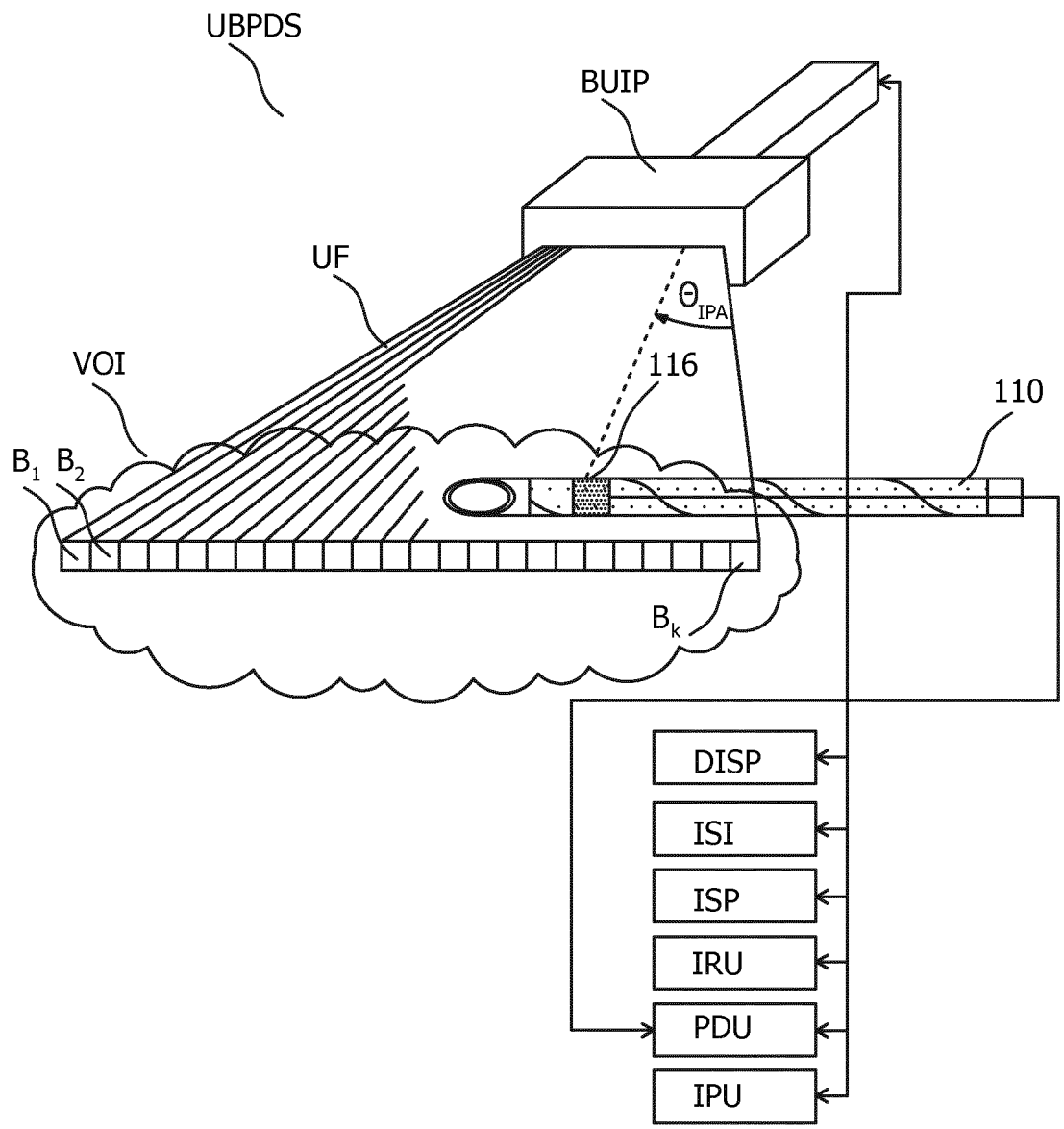
FIG. 17 illustrates an exemplary ultrasound-based position determination system UBPDS in which the interventional device may be used.

FIG. 17 illustrates an exemplary ultrasound-based position determination system UBPDS in which the interventional device may be used. In FIG. 17, ultrasound-based position determination system UBPDS includes a beamforming ultrasound imaging probe BUIP which is in communication with image reconstruction unit IRU, imaging system processor ISP, imaging system interface ISI and display DISP. Together, units BUIP, IRU, ISP, ISI and DISP form a conventional ultrasound imaging system. The units IRU, ISP, ISI and DISP are conventionally located in a console that is in wired or wireless communication with beamforming ultrasound imaging probe BUIP. Some of units IRU, ISP, ISI and DISP may alternatively be incorporated within beamforming ultrasound imaging probe BUIP as for example in the Philips Lumify™ ultrasound imaging system. Beamforming ultrasound imaging probe BUIP generates ultrasound field UF. In FIG. 17, a 2D beamforming ultrasound imaging probe BUIP is illustrated that includes a linear ultrasound transceiver array that transmits and receives ultrasound energy within an ultrasound field UF which intercepts volume of interest VOI. The ultrasound field is fan-shaped in FIG. 17 and includes multiple ultrasound beams $B_{1...k}$ that together provide the illustrated image plane. Note that whilst a fan-shaped beam is illustrated in FIG. 17 for the purposes of illustration the invention is not limited to a particular shape of ultrasound field. Beamforming ultrasound imaging probe BUIP may also include electronic driver and receiver circuitry (not shown) that is configured to amplify and/or to adjust the phase of signals it transmits of receives in order to generate and detect ultrasound signals in ultrasound beams $B_{1...k}$.

In-use the above-described conventional ultrasound imaging system is operated in the following way. An operator may plan an ultrasound procedure via imaging system interface ISI. Once an operating procedure is selected, imaging system interface ISI triggers imaging system processor ISP to execute application-specific programs that generate and interpret the signals transmitted to and detected by beamforming ultrasound imaging probe BUIP. A memory (not shown) may be used to store such programs. The memory may for example store ultrasound beam control software that is configured to control the sequence of ultrasound signals transmitted by and/or received by beamforming ultrasound imaging probe BUIP. Image reconstruction unit IRU, which may alternatively form part of imaging system processor ISP. Image reconstruction unit IRU provides a reconstructed ultrasound image corresponding to ultrasound field UF of beamforming ultrasound imaging probe BUIP. IRU thereby provides an image corresponding to the image plane defined by ultrasound field UF and which thus intercepts volume of interest VOI. The image is subsequently displayed on display DISP. The reconstructed image may for example be an ultrasound Brightness-mode "B-mode" image, otherwise known as a "2D mode" image, a "C-mode" image or a Doppler mode image, or indeed any ultrasound image.

Also shown in FIG. 17 is interventional device 110, exemplified by a medical needle, which includes piezoelectric transducer 116. In this exemplary application of the interventional device, interventional device 110, or more specifically piezoelectric transducer 116 disposed thereon, may be tracked respective ultrasound field UF based on signals provided by position determination unit PDU and icon providing unit IPU. These units are in communication with one another and units BUIP, IRU, ISP, ISI and DISP, i.e. the conventional ultrasound imaging system as illustrated by the interconnecting arrows. One or more of units PDU and IPU may be incorporated within a memory or a processor of the conventional ultrasound imaging system.

In-use, the position of piezoelectric transducer 116 is computed respective ultrasound field UF by position determination unit PDU based on ultrasound signals transmitted between beamforming ultrasound imaging probe BUIP and piezoelectric transducer 116.

In one configuration piezoelectric transducer 116 is a detector that receives ultrasound signals corresponding to beams $B_{1...k}$. Position determination unit PDU identifies the position of piezoelectric transducer 116 by correlating the ultrasound signals emitted by beamforming ultrasound imaging probe BUIP with the ultrasound signals detected by piezoelectric transducer 116. Icon providing unit IPU subsequently provides an icon in the reconstructed ultrasound image based on the computed position of piezoelectric transducer 116. More specifically the correlation determines the best fit position of piezoelectric transducer 116 respective ultrasound field UF based on i) the amplitudes of the ultrasound signals corresponding to each beam $B_{1...k}$ that are detected by piezoelectric transducer 116, and based on ii) the time delay, i.e. time of flight, between emission of each beam $B_{1...k}$ and its detection by piezoelectric transducer 116. This may be illustrated as follows. When piezoelectric transducer 116 is in the vicinity of ultrasound field UF, ultrasound signals from the nearest of beams $B_{1...k}$ the transducer will be detected with a relatively larger amplitude whereas more distant beams will be detected with relatively smaller amplitudes. Typically the beam that is detected with the largest amplitude is identified as the one that is closest to piezoelectric transducer 116. This beam defines the in-plane angle $\theta_{IPA}$ between beamforming ultrasound imaging probe BUIP and piezoelectric transducer 116. The corresponding range depends upon the time delay, i.e. the time of flight, between the emission of the largest-amplitude beam $B_{1...k}$ and its subsequent detection. The range is determined by multiplying the time delay by the speed of ultrasound propagation. Thus, the range and corresponding in-plane angle $\theta_{IPA}$ of the beam detected with the largest amplitude can be used to identify the best-fit position of piezoelectric transducer 116 respective ultrasound field UF.

In another configuration piezoelectric transducer 116 may be an emitter that emits one or more ultrasound pulses. Such pulses may for example be emitted during tracking frames that are interleaved between the imaging frames of the conventional ultrasound imaging system. In such a tracking frame, beamforming ultrasound imaging probe BUIP may operate in a receive-only mode in which it listens for ultrasound signals originating from the vicinity of ultrasound field UF. Beamforming ultrasound imaging probe BUIP is thus configured as a one-way receive-only beamformer during such tracking frames. Position determination unit PDU identifies from which beam of virtual beams $B_1 \ldots k$ the pulse(s) originated by applying delays to the receiver elements of beamforming ultrasound imaging probe BUIP. The delays correspond to each of virtual beams $B_1 \ldots k$. As in the detector configuration above, position determination unit PDU may use a correlation procedure that, based on the maximum amplitude and time of flight, identifies the closest beam $B_1 \ldots k$ to the position at which the ultrasound signal was emitted, and the corresponding range to piezoelectric transducer 116. Icon providing unit IPU subsequently provides an icon in the reconstructed ultrasound image based on the identified position of piezoelectric transducer 116. Thus, when piezoelectric transducer 116 is an ultrasound emitter, a correlation procedure may again be used to determine the best-fit position of piezoelectric transducer 116 respective ultrasound field UF for each tracking frame.

In another configuration piezoelectric transducer 116 may be configured to act as both a receiver and an emitter. In this configuration piezoelectric transducer 116 may be triggered to emit one or more ultrasound pulses upon receipt of an ultrasound signal from beamforming ultrasound imaging probe BUIP. In this way the pulse(s) emitted by piezoelectric transducer 116 during an imaging mode are received by beamforming ultrasound imaging probe BUIP appear as an echo in the reconstructed ultrasound at an in-plane angular position, i.e. in an image line, that corresponds to the relevant beam $B_1 \ldots k$. Piezoelectric transducer 116 thus appears as a bright spot in the reconstructed image. Position determination unit PDU may subsequently identify this bright spot in the reconstructed image and thus compute a position of piezoelectric transducer 116 respective ultrasound field UF.

In the above-described ultrasound-based position determination system UBPDS the dependence of the sensitivity, or emission profile, of piezoelectric transducer 116 on rotational angle of the interventional device may impact its positioning respective ultrasound field UF. Thereto, the above-described interventional device has the aforementioned benefits. Optionally, icon providing unit IPU of ultrasound-based position determination system UBPDS may be further configured to indicate in the reconstructed ultrasound image a detected magnitude of the ultrasound signals transmitted between the beamforming ultrasound imaging probe BUIP and the piezoelectric transducer 116. The magnitude may be expressed in numerical or graphical format, and may be expressed in relation to a maximum expected magnitude. This may be useful in determining a rotational orientation of interventional device 110 respective ultrasound field UF.

It is also to be appreciated that the exemplified beamforming ultrasound imaging probe BUIP is only one example of a beamforming ultrasound imaging system in which interventional device 116 may be used. Interventional device 116 also finds application in ultrasound-based position determination systems that include other types of 2D or 3D beamforming ultrasound imaging systems. These may include for example a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe. Moreover, it is to be appreciated that the invention also finds application in other sensing and actuation applications in the medical field beyond position determination.

In summary, an interventional device has been described that includes an elongate shaft and a transducer strip. The transducer strip includes a first edge and an opposing second edge. The first edge and the second edge are separated by a width dimension, and the first edge and the second edge each extend along a length direction of the transducer strip. The transducer strip also includes a piezoelectric transducer that extends along a transducer direction that forms an acute angle with respect to the length direction. The transducer strip is wrapped in the form of a spiral around the elongate shaft of the interventional device such that the piezoelectric transducer forms a band around the elongate shaft. The width dimension is defined such that the adjacent first and second edges of consecutive turns of the spiral abut or overlap one another.

Various implementations and options have been described in relation to the interventional device, and it is noted that these may be combined to achieve further advantageous effects.

The invention claimed is:

1. An interventional device comprising:
   an elongate shaft;
   a transducer strip comprising:
      a first edge and an opposing second edge separated by a width dimension, the first edge and the second edge each extending along a length direction of the transducer strip, and
      a piezoelectric transducer disposed on a portion of the transducer strip and extending on the transducer strip along a transducer direction that forms an acute angle with respect to the length direction of the transducer strip,
   wherein the transducer strip is wrapped in a form of a spiral around the elongate shaft of the interventional device, such that the piezoelectric transducer disposed on the portion of the transducer strip forms a band around the elongate shaft;
   and wherein the width dimension is defined such that the first edge and the second opposing edge in consecutive turns of the spiral abut or overlap one another.

2. The interventional device according to claim 1, wherein:
   the elongate shaft extends along a shaft axis;
   the piezoelectric transducer is defined by a straight line; and
   the transducer direction is arranged perpendicularly to the shaft axis, such that the band lies in a plane having a normal that is co-axial with the shaft axis.

3. The interventional device according to claim 1, wherein:
   the elongate shaft extends along a shaft axis;
   the piezoelectric transducer comprises a sinusoidal shape that oscillates about a centerline;
   the centerline is a straight line defined by the transducer direction; and the transducer direction is arranged perpendicularly to the shaft axis, such that the band lies in a plane having a normal that is tilted with respect to the shaft axis.

4. The interventional device according to claim 1, wherein:
the piezoelectric transducer comprises a first end and a second end; and
the band formed by the wrapped transducer strip includes either i) an overlap or ii) a space between the first end and the second end.

5. The interventional device according to claim 4, wherein:
the first end is disposed adjacent the first edge;
wherein the second end is disposed adjacent the second edge; and
the piezoelectric transducer includes at least one of a first gap between the first end of the piezoelectric transducer and the first edge of the transducer strip or a second gap between the second end of the piezoelectric transducer and the second edge of the transducer strip, and the space comprises at least a portion of at least one of the first gap or at least a portion of the second gap.

6. The interventional device according to claim 4, further comprising:
a bevel defined by an ellipse having a major axis and a minor axis;
wherein the major axis defines two major rotational angles at two opposing positions around a circumference of the elongate shaft and the minor axis defines two minor rotational angles at two opposing positions around the circumference of the elongate shaft; and
wherein the overlap or the space includes a midpoint that is aligned rotationally around the circumference of the elongate shaft at one of the major rotational angles or at one of the minor rotational angles.

7. The interventional device according to claim 1, wherein:
the transducer strip further comprises a first electrical conductor; and
the first electrical conductor is in electrical contact with the piezoelectric transducer and extends along the length direction of the transducer strip.

8. The interventional device according to claim 7, wherein:
the piezoelectric transducer further comprises a first electrode; and
the first electrical conductor is in electrical contact with the piezoelectric transducer via the first electrode.

9. The interventional device according to claim 8, wherein:
the piezoelectric transducer further comprises a second electrode that is in electrical contact with the conductive elongate shaft; and
the elongate shaft of the interventional device is formed from a conductive material.

10. The interventional device according to claim 8, wherein:
the piezoelectric transducer further comprises a second electrode; and
the transducer strip further comprises a second electrical conductor that extends along the length direction of the transducer strip and is in electrical contact with the piezoelectric transducer via the second electrode.

11. The interventional device according to claim 10, wherein:
the interventional device further comprises a distal end and a proximal end and the piezoelectric transducer is disposed towards the distal end of the interventional device; and
the first electrical conductor and the second electrical conductor each extend along the length direction of the transducer strip to the proximal end of the interventional device at which the first electrical conductor and the second electrical conductor are both exposed along at least a portion of the elongate shaft of the interventional device to make electrical contact to an external connector.

12. The interventional device according to claim 11, wherein:
the transducer strip comprises a polymer substrate that is arranged innermost with respect to the interventional device and a polymer superstrate that is arranged outermost with respect to the elongate shaft of the interventional device; and
towards the distal end of the interventional device, a) the first electrical conductor and the second electrical conductor are sandwiched between the polymer substrate and the polymer superstrate and b) the polymer superstrate includes at least one opening configured to expose at least one of the first electrical conductor or the second electrical conductor along the at least a portion of the elongate shaft of the interventional device.

13. The interventional device according to claim 12, wherein:
towards the proximal end of the interventional device, the polymer superstrate includes a first opening that exposes the first electrical conductor and a second opening that exposes the second electrical conductor; the first opening and the second opening being staggered along the length direction of the transducer strip, such that the first electrical conductor and the second electrical conductor are exposed at axially-separated axial positions along the elongate shaft of the interventional device and at the same rotational angle around a circumference of the elongate shaft.

14. An ultrasound-based position determination system comprising:
the interventional device according to claim 1;
a beamforming ultrasound imaging probe configured to generate an ultrasound field;
an image reconstruction processor configured to provide a reconstructed ultrasound image corresponding to the ultrasound field of the beamforming ultrasound imaging probe;
a position determination processor configured to compute a position of the piezoelectric transducer of the interventional device respective the ultrasound field based on ultrasound signals transmitted between the beamforming ultrasound imaging probe and the piezoelectric transducer; and
an icon providing processor configured to provide an icon in the reconstructed ultrasound image based on the computed position of the piezoelectric transducer.

15. The ultrasound-based position determination system according to claim 14, wherein the icon providing processor is configured to indicate in the reconstructed ultrasound image a detected magnitude of the ultrasound signals transmitted between the beamforming ultrasound imaging probe and the piezoelectric transducer.

* * * * *